US005929122A

United States Patent [19]

Reimann

[11] Patent Number: 5,929,122

[45] Date of Patent: Jul. 27, 1999

[54] COMBINATION PREPARATION CONTAINING TRAMADOL AND A CALCIUM CHANNEL ANTAGONIST

[75] Inventor: Wolfgang Reimann, Aachen, Germany

[73] Assignee: Gruenenthal GmbH, Aachen, Germany

[21] Appl. No.: 08/942,048

[22] Filed: Oct. 1, 1997

[30] Foreign Application Priority Data

Oct. 9, 1996 [DE] Germany ........................... 196 41 576

[51] Int. Cl.[6] ........................ A61K 31/135; A61K 31/55; A61K 31/495; A61K 31/44

[52] U.S. Cl. .......................... 514/646; 514/211; 514/255; 514/356; 514/654

[58] Field of Search .................................... 514/646, 356, 514/211, 654, 255

[56] References Cited

FOREIGN PATENT DOCUMENTS 0 546 676 A1 6/1993 European Pat. Off. .
WO 93/04675 3/1993 WIPO .

OTHER PUBLICATIONS

Miranda et al, Chemical Abstracts, vol. 117, abstract No. 184662. 1992.

Saha et al, Chemical Abstracts, vol. 116, abstract No. 34330, 1990.

Al–Humayyd, Chemical Abstracts, vol. 114, abstract No. 55721, 1991.

Enrique Contreras, Lya Tamayo and Marco Amigo, "Calcium channel antagonists increase morphine–induced analgesia and antagonize morphine tolerance," *European Journal of Pharmacology*, No. 148 (1988) pp. 463–466.

Esperanza Del Pozo, Gerardo Caro and José M. Baeyens, "Analgesic effects of several calcium channel blockers in mice," *European Journal of Pharmacology*, No. 137 (1988) pp. 155–160.

Bormann et al., "Do Ca–Channel Blockers Have Analgesic Effects?", *Fortschr. Anaesth.*, 1:5–10 (1987).

Jurna et al., "Differential Effects of Morphine and Opioid Analgesics on A and C Fibre–Evoked Activity in Ascending Axons of the Rat Spinal Cord", *Brain Research*, 171 (1979) 573–576.

Reimann et al., "Spinal Antionciception by Morphine in Rats is Antagonised by Galanin Receptor Antagonists", *Archives of Pharmacology*, (1994) 350:380–386.

*Primary Examiner*—William R. A. Jarvis
*Attorney, Agent, or Firm*—Evenson, McKeown, Edwards & Lenahan, P.L.L.C.

[57] ABSTRACT

A pharmaceutical combination preparation, particularly for the treatment of pain, which contains a combination of the pain killer tramadol with at least one calcium channel antagonist, and a method of treating pain by administering to a patient suffering therefrom an analgesically effective combination of tramadol and at least one calcium channel antagonist.

18 Claims, No Drawings

COMBINATION PREPARATION CONTAINING TRAMADOL AND A CALCIUM CHANNEL ANTAGONIST

FIELD OF THE INVENTION

The present invention relates to a pharmaceutical combination preparation, particularly for the treatment of pain, which contains a combination of the pain-killer tramadol and a calcium channel antagonist, and to a method of treating pain using such a combination preparation.

BACKGROUND OF THE INVENTION

Due to their strong analgesic effect, opioids are used for the alleviation of moderately severe to the most severe acute pain. However, one considerable disadvantage of the use of opioids is the severe side effects associated therewith. Thus they frequently have effects on the gastrointestinal tract, such as obstipation (?), and moreover give rise to respiratory depression, and, on repeated use, to dependency which can lead to misuse. Furthermore, the development of tolerance is a disadvantageous effect.

It has been known for many years that the analgesic effect of opioids is enhanced by the simultaneous administration of organic calcium channel antagonists (*Fortschr. Anaesth.* 1987, 5). Calcium channel antagonists can be classified into those of the dihydropyridine, benzothiazepine and phenylalkylamine types. They are usually employed for the treatment of cardiovascular disease conditions such as high blood pressure, arrhythmia or angina pectoris. The mode of action of these substances act is based on the selective suppression of the $Ca^{2+}$ flux in the $Ca^{2+}$ channels of the heart and of the peripheral vascular system. Calcium channels with a high affinity for calcium channel antagonists have also been detected in the brain, so that a central effect of calcium channel antagonists appears probable.

Due to the enhancement of the anti-nociceptive effect of opioids by means of calcium channel antagonists, lower doses of the opioid can be administered for the same analgesic effect. The aforementioned side effects can thereby be reduced. On continued administration, however, the occurrence of dependency, respiratory depression and obstipation (?) must be reckoned with despite these smaller amounts of opioids. Due to the high analgesic efficacy of opioids, however, their use for the treatment of pain cannot to this day be dispensed with.

SUMMARY OF THE INVENTION

An underlying object of the present invention is therefore to provide a new pharmaceutical composition which contains an analgesic which can be combined with a calcium channel antagonist.

Another object of the invention is to provide a new analgesic pharmaceutical composition which can be administered in small doses.

It is also an object of the invention to provide an analgesic pharmaceutical composition which does not have the disadvantages of opioids described above.

A further object of the invention is to provide a method of analgesic treatment which avoids the disadvantages of treatment with opiates.

These and other objects are achieved in accordance with a first aspect of the present invention by providing an analgesic combination preparation comprising an analgesically effective combination of tramadol in the form of a free base or of a physiologically compatible salt, and at least one calcium channel antagonist.

In accordance with a further aspect of the invention, the objects are achieved by providing a method of treating pain in a mammal comprising concurrently administering to said mammal an analgesically effective combination of tramadol in the form of a free base or of a physiologically compatible salt, and at least one calcium channel antagonist.

DETAILED DESCRIPTION OF THE PREFERRED EMBODIMENTS

It has been found that the analgesic effect of tramadol is enhanced by using a combination therapy comprising tramadol or pharmaceutically compatible salts thereof with a calcium channel antagonist.

Accordingly, the present invention relates to a combination preparation, containing tramadol in the form of the free base or of a physiologically compatible salt and at least one calcium channel antagonist in a separate or joint formulation.

Tramadol is the INN name for the centrally acting analgesic (1RS,2RS)-2-[(dimethylamino)methyl]-1-(3-methoxyphenyl-cyclohexanol). It is preferably administered in the form of its hydrochloride. A racemate of (+) and (−) tramadol is customarily used. However, it is also possible to administer only one of the two enantiomers each time.

The combination preparations according to the invention cause no significant respiratory depression and have a low potential for the development of tolerance, dependency and misuse. The range of effectiveness of the combination preparations extends into neuropathy.

Suitable calcium channel antagonists include those of the dihydropyridine, benzothiazepine and phenylalkylamine types. Examples of calcium channel antagonists from the dihydropyridine group include nimodipine, nicardipine and nifedipine. Examples of calcium channel antagonists of the benzothiazepine type include diltiazem. Examples of calcium channel antagonists of the phenylalkylamine type include verapamil, gallopamil, flunarizine and cinnarizine.

In the combination therapy to which the present invention relates, tramadol is preferably used in combination with only one calcium channel antagonist. It is also possible, however, to use two or more of these antagonists. If a plurality of calcium channel antagonists is used, these may be from one type class only or from two or more different type classes of those mentioned above.

The active ingredients of the combination preparation according to the invention can be administered as a joint formulation or separately.

In addition to tramadol in the form of the free base or in the form of a physiologically compatible salt and one or more calcium channel antagonists, combination preparations according to the invention for co-administration (joint administration) of active ingredients usually contain support materials, fillers, solvents, diluents, colorants and/or binders. The selection of these adjuvant substances and of the amounts to be used depend upon whether the pharmaceutical composition according to the invention is to be applied orally, intravenously, intraperitoneally, intradermally, intramuscularly, intranasally, buccally or locally, for example for infections of the skin, of the mucous membranes and of the eyes. Preparations in the form of tablets, dragees, capsules, granules, drops, juices and syrups are suitable for oral administration. Solutions, suspensions, readily reconstitutable dry preparations and sprays are suitable for parenteral and topical administration and for administration by inhalation. Combination preparations according to the invention as a deposit in a dissolved form or in a transdermal patch, optionally with the addition of agents which promote dermal penetration, are examples of suitable percutaneous forms of preparation. The active ingredients can be released in a delayed manner from forms of preparations which can be administered orally or percutaneously.

When the active ingredients are administered separately, the forms of administration for tramadol and calcium channel antagonists are generally used which are customarily permitted and which are familiar to one skilled in the art. Known forms of administration for tramadol include tablets, delayed-action tablets, drops, capsules, suppositories, infusion solutions and injection solutions, particularly as ready-to-use syringes, for example.

Calcium channel antagonists can be administered, for example, as an injection or infusion solution, as drops, capsules, barrier film- or delayed-action tablets, delayed-action capsules or dragees. Tablets, capsules, drops and infusion solutions are preferred.

The amounts of active ingredient to be administered to patients varies depending on the weight of the patient, on the type of administration, on the indication and on the degree of severity of the illness. From 10 mg to 800 mg, preferably from 20 mg to 400 mg, of tramadol as the hydrochloride, or the corresponding amount of another physiologically compatible salt or of the free base, is usually administered as the daily dose, both for the separate and for the joint formulation. The corresponding amount of calcium channel antagonist ranges from a quarter of the minimum effective dose up to the maximum daily dose (given on the consignment label), preferably from a quarter of the minimum effective dose up to a half of the maximum daily dose.

Due to the combination of the two groups of active ingredients, the amount of tramadol which is necessary for the suppression of pain can be considerably reduced. A combination preparation according to the invention is typically used for the treatment of moderately severe to severe acute or chronic pain.

EXAMPLES

Example 1

The anti-nociceptive effect of tramadol (as the hydrochloride) and calcium channel antagonists was investigated separately and in solution together. For this purpose, the respective active ingredients in solution were injected intrathecally (near the spinal cord) into rats, and a tail flick test was performed 10 minutes after injection. A focused light beam was directed on to the tails of the rats in order to simulate a pain stimulus. The results listed below represent the period of latency until the tail was pulled away, expressed as a percentage of the maximum value which could be attained (MPE). The number of animals per group, n, was 10 (n=10). The methodology employed is described by Reimann et al. in *Naunyn-Schmiedeberg's Arch Pharmacol.* 350, 380 (1994).

| Test Substance(s) | MPE |
|---|---|
| tramadol (6 μg) | 9.1 ± 3.2 |
| tramadol (12 μg) | 15.3 ± 6.3 |
| nimodipine (10 μg) | 17.3 ± 8.2 |
| nimodipine (10 μg) + tramadol (6 μg) | 55.6 ± 9.4 |
| nimodipine (10 μg) + tramadol (12 μg) | 70.6 ± 8.8 |
| diltiazem (10 μg) | 4.3 ± 5.1 |
| diltiazem (10 μg) + tramadol (6 μg) | 51.9 ± 6.4 |

-continued

| Test Substance(s) | MPE |
|---|---|
| diltiazem (10 μg) + tramadol (12 μg) | 64.4 ± 8.6 |
| verapamil (20 μg) | 13.9 ± 9.3 |
| verapamil (20 μg) + tramadol (6 μg) | 31.5 ± 9.9 |
| verapamil (20 μg) + tramadol (12 μg) | 39.2 ± 9.3 |

The results show that the simultaneous administration of tramadol hydrochloride and calcium channel antagonists results in an increase in the anti-nociceptive effect of tramadol.

Example 2

After electrical stimulation of the predominantly sensory sural nerves, the nerve impulses ascending to the brain in the spinal cord of rats were measured. The impulses of the Ab and Ag fibers could be separated from those of the purely sensory C fibers due to the different conduction rates. The experiments were performed essentially in accordance with the methods described by Jurna and Heinz [*Brain Res.,* Vol. 171, pp. 573–576 (1979)]. The results show the percentage change in C fibre activity in the spinal cord caused by the administration of the active ingredients (administered intravenously; separately or together). The measurement was made 60 minutes after the intravenous injection of the substances.

| Test Substance(s) | % Change | Number of Experiments |
|---|---|---|
| tramadol (14.6 mg/kg) | −1.9 ± 10.3 | 3 |
| diltiazem (2.15 mg/kg) | 5.4 ± 10.3 | 5 |
| diltiazem (2.15 mg/kg) + tramadol (14.6 mg/kg) | −18.6 ± 12.1 | 5 |
| verapamil (0.1 mg/kg) | −13.3 ± 1.2 | 5 |
| verapamil (0.1 mg/kg) + tramadol (14.6 mg/kg) | −25.5 ± 10.7 | 5 |

The results show that tramadol (as the hydrochloride) together with a calcium channel antagonist in a joint formulation has an enhanced anti-nociceptive effect.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. An analgesic combination preparation, comprising an analgesically effective combination of tramadol in the form of a free base or of a physiologically compatible salt, and at least one calcium channel antagonist.

2. A combination preparation according to claim 1, comprising individual doses of tramadol and of the calcium channel antagonist packaged together for concurrent separate administration.

3. A combination preparation according to claim 1, wherein the tramadol and the calcium channel antagonist are combined into a single pharmaceutical composition for simultaneous co-administration.

4. A combination preparation according to claim 1, wherein the tramadol is in the form of a physiologically compatible salt.

5. A combination preparation according to claim 4, wherein the tramadol is in the form of tramadol hydrochloride.

6. A combination preparation according to claim 1, which comprises a single calcium channel antagonist.

7. A combination preparation according to claim 1, comprising from 10 mg to 800 mg of tramadol hydrochloride or an equivalent amount of another physiologically compatible salt or of tramadol free base.

8. A combination preparation according to claim 7, comprising from 20 mg to 400 mg of tramadol hydrochloride or an equivalent amount of another physiologically compatible salt or of tramadol free base.

9. A combination preparation according to claim 1, wherein the calcium channel antagonist is contained in an amount in the range from a quarter of the minimum effective dose up to the maximum daily dose of the respective calcium channel antagonist.

10. A combination preparation according to claim 9, wherein the calcium channel antagonist is contained in an amount in the range from a quarter of the minimum effective dose up to half the maximum daily dose of the respective calcium channel antagonist.

11. A combination preparation according to claim 1, wherein the at least one calcium channel antagonist is selected from the group consisting of nimodipine, nicardipine, nifedipine, diltiazem, verapamil, gallopamil, flunarizine and cinnarizine.

12. A method of treating pain in a mammal comprising concurrently administering to said mammal an analgesically effective combination of tramadol in the form of a free base or of a physiologically compatible salt, and at least one calcium channel antagonist.

13. A method according to claim 12, wherein the tramadol is administered in the form of tramadol hydrochloride.

14. A method according to claim 12, wherein the tramadol and the calcium channel antagonist are co-administered as a joint formulation.

15. A method according to claim 12, wherein from 10 mg to 800 mg of tramadol hydrochloride or an equivalent amount of another physiologically compatible salt or of tramadol free base are administered.

16. A method according to claim 15, wherein from 20 mg to 400 mg of tramadol hydrochloride or an equivalent amount of another physiologically compatible salt or of tramadol free base are administered.

17. A method according to claim 12, wherein the calcium channel antagonist is administered in an amount in the range from a quarter of the minimum effective dose up to the maximum daily dose of the respective calcium channel antagonist.

18. A method according to claim 17, wherein the calcium channel antagonist is administered in an amount in the range from a quarter of the minimum effective dose up to half the maximum daily dose of the respective calcium channel antagonist.

* * * * *